US011364503B2

(12) United States Patent
Shkolnikov et al.

(10) Patent No.: US 11,364,503 B2
(45) Date of Patent: Jun. 21, 2022

(54) DIELECTROPHORESIS SEPARATORS WITH CELL EJECTION DEVICES

(71) Applicant: HEWLETT-PACKARD DEVELOPMENT COMPANY, L.P., Houston, TX (US)

(72) Inventors: Viktor Shkolnikov, Palo Alto, CA (US); Kenneth Ward, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 986 days.

(21) Appl. No.: 16/077,362

(22) PCT Filed: Jul. 17, 2017

(86) PCT No.: PCT/US2017/042373
§ 371 (c)(1),
(2) Date: Aug. 10, 2018

(87) PCT Pub. No.: WO2019/017875
PCT Pub. Date: Jan. 24, 2019

(65) Prior Publication Data
US 2021/0205809 A1 Jul. 8, 2021

(51) Int. Cl.
*B01L 3/00* (2006.01)
*B01L 3/02* (2006.01)
(Continued)

(52) U.S. Cl.
CPC ....... *B01L 3/502761* (2013.01); *B01L 3/0268* (2013.01); *B03C 5/005* (2013.01);
(Continued)

(58) Field of Classification Search
None
See application file for complete search history.

(56) References Cited

U.S. PATENT DOCUMENTS 6,432,630 B1 * 8/2002 Blankenstein ......... B01D 57/02
435/4
6,540,895 B1 * 4/2003 Spence ............. B01L 3/502761
204/450

(Continued)

FOREIGN PATENT DOCUMENTS

WO 2016122643 A1 8/2016
WO 2016193758 A1 12/2016

OTHER PUBLICATIONS

Kaler et al., "Liquid Dielectrophoresis and Surface Microfluidics", Biomicrofluidics, vol. 4, Issue No. 2, Retrieved from Internet—https://www.ncbi.nlm.nih.gov/pmc/articles/PMC2917863/, 2010, 11 Pages.

*Primary Examiner* — Brian R Gordon
(74) *Attorney, Agent, or Firm* — Fabian VanCott

(57) ABSTRACT

A microfluidic device may, in an example, include at least one microfluidic channel, a dielectrophoresis separator to separate a plurality of cells passing within the at least one microfluidic channel, and a thermal resistor to eject at least one cell from the microfluidic device. A cassette may, in an example, include a die coupled to a substrate of the cassette, the die including at least one microfluidic channel, a dielectrophoresis separator along the microfluidic channel to separate a plurality of cells passing within the microfluidic channel, and an ejection device to eject at least one of the plurality of cells into an assay well.

19 Claims, 6 Drawing Sheets

(51) Int. Cl.
*B03C 5/00* (2006.01)
*B03C 5/02* (2006.01)

(52) U.S. Cl.
CPC ....... *B03C 5/022* (2013.01); *B01L 2200/0652* (2013.01); *B01L 2300/0816* (2013.01); *B01L 2400/0424* (2013.01); *B01L 2400/0442* (2013.01); *B03C 2201/26* (2013.01)

(56) References Cited

U.S. PATENT DOCUMENTS

| | | | |
|---|---|---|---|
| 7,138,269 B2 | 11/2006 | Blankenstein | |
| 7,294,249 B2 | 11/2007 | Gawad et al. | |
| 7,294,503 B2* | 11/2007 | Quake | B01L 3/502784 |
| | | | 436/63 |
| 7,658,829 B2 | 2/2010 | Kanagasabapathi et al. | |
| 8,834,793 B2 | 9/2014 | Koltay et al. | |
| 9,555,421 B2 | 1/2017 | Sato et al. | |
| 2002/0058332 A1* | 5/2002 | Quake | B01L 3/502715 |
| | | | 435/288.5 |
| 2005/0009101 A1 | 1/2005 | Blackbum | |
| 2005/0202504 A1 | 9/2005 | Anderson et al. | |
| 2006/0223178 A1* | 10/2006 | Barber | C12M 35/06 |
| | | | 435/372 |
| 2009/0139866 A1 | 6/2009 | Nam et al. | |
| 2010/0015614 A1* | 1/2010 | Beer | B01L 3/502792 |
| | | | 435/6.12 |
| 2012/0085649 A1* | 4/2012 | Sano | B03C 5/005 |
| | | | 204/547 |
| 2012/0103817 A1* | 5/2012 | Omori | B01L 3/502761 |
| | | | 204/643 |
| 2012/0264646 A1* | 10/2012 | Link | B01F 5/0653 |
| | | | 506/11 |
| 2012/0298511 A1 | 11/2012 | Yamamoto | |
| 2014/0073027 A1* | 3/2014 | Dholakia | C12N 13/00 |
| | | | 435/173.6 |
| 2014/0227777 A1* | 8/2014 | Choi | B01L 3/502761 |
| | | | 435/309.1 |
| 2014/0255270 A1* | 9/2014 | Satsanarukkit | B01L 3/502707 |
| | | | 427/226 |
| 2014/0262787 A1* | 9/2014 | Molho | B01L 3/502761 |
| | | | 204/547 |
| 2015/0093743 A1* | 4/2015 | Sadri | C12Q 1/24 |
| | | | 435/5 |
| 2016/0231274 A1* | 8/2016 | Tirapu Azpiroz | G01N 27/44713 |
| 2016/0370266 A1* | 12/2016 | White | B03C 5/026 |
| 2017/0007997 A1* | 1/2017 | Lal | B01L 3/502784 |
| 2017/0128941 A1* | 5/2017 | Sadri | B01L 3/502738 |
| 2018/0024155 A1* | 1/2018 | McGuinness | G01N 35/08 |
| | | | 422/507 |
| 2018/0203005 A1* | 7/2018 | Kon | G01N 35/08 |
| 2018/0355407 A1* | 12/2018 | Utharala | B01L 3/502738 |
| 2019/0345488 A1* | 11/2019 | Soumillon | B01J 19/0046 |

* cited by examiner

DIELECTROPHORESIS SEPARATORS WITH CELL EJECTION DEVICES

BACKGROUND

Infectious diseases and other medical conditions affect human life on a continual basis. The life sciences research and associated diagnostic industries have made developments directed to detecting the presence of pathogens in blood or other bodily fluids as well as detect certain types of cells in body fluids in order to diagnose a patient's illness.

BRIEF DESCRIPTION OF THE DRAWINGS

The accompanying drawings illustrate various examples of the principles described herein and are part of the specification. The illustrated examples are given merely for illustration, and do not limit the scope of the claims.

Figure 1:
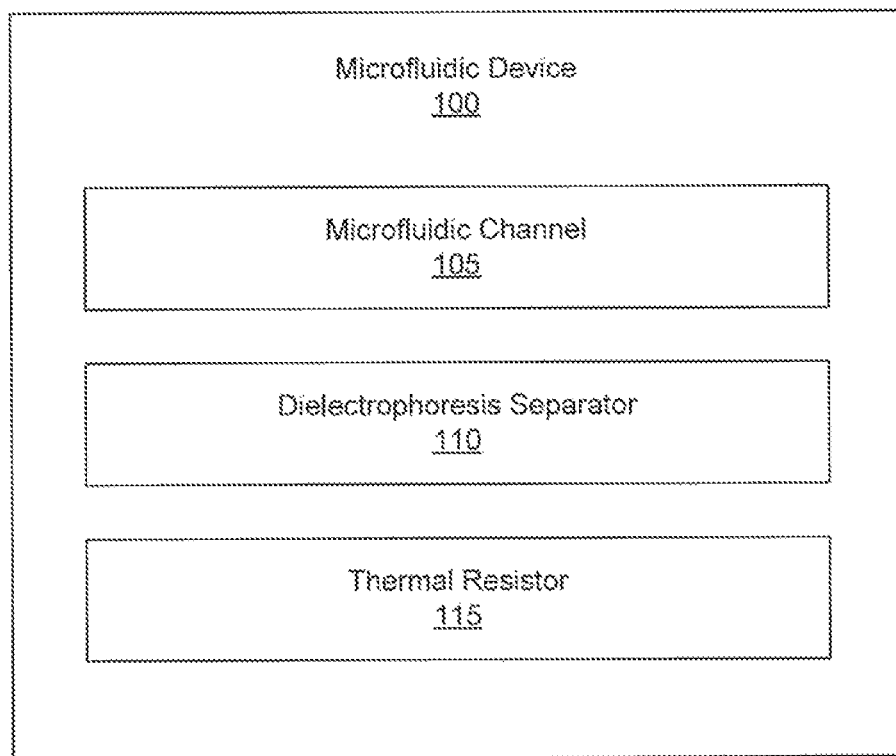
FIG. 1 is a block diagram of a microfluidic device according to an example of the principles described herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

Human interaction during life science research and diagnostic processes may lead to mistakes in those processes. Such mistakes may decrease the likelihood of scientific breakthroughs and increase the likelihood of misdiagnosis of patient's illnesses. Further, with human interaction, these processes may prove tedious thereby increasing the costs associated with these processes as well as increase the time spent completing the processes. Automation of these processes, however, limits mistakes, time, and costs.

Instruments and tools used in life science research and diagnostic processes have been developed to increase efficiency, decrease costs, and decrease time spent conducting this research or completing diagnosis. However, these instruments and tools do not allow for obtaining single and relatively rare types of cells within a sample. Specifically, these tools have yet to separate from a sample these types of cells. Further, any cell separation devices may not be capable of separating certain types of cells and delivering them, individually, into an assay plate that includes an array of wells to house the individual cells. By being able to conduct such a cell-by-cell analysis allows a user to determine better how cells work on the individual level as well as how the heterogeneity of such behavior contributes to the function of the overall tissue. Consequently, the cells may be separated based on the physical properties and then placed in the individual containers for downstream analysis such as sequencing of DNA and RNA or mass spectroscopic analysis of proteins.

The present specification describes a microfluidic device that includes at least one microfluidic channel, a dielectrophoresis separator to separate a plurality of cells passing within the at least one microfluidic channel, and a thermal resistor to eject at least one cell from the microfluidic device.

The present specification also describes a cassette that includes a die coupled to a substrate of the cassette, the die including at least one microfluidic channel, a dielectrophoresis separator along the microfluidic channel to separate a plurality of cells passing within the microfluidic channel, and an ejection device to eject at least one of the plurality of cells into an assay well.

The present specification further describes a fluid ejection system that includes an electrical dispensing device and a cassette comprising at least one dispense head, the at least one dispense head including at least one microfluidic channel, a dielectrophoresis separator to separate a plurality of cells passing within the at least one microfluidic channel, and a thermal resistor to eject at least one cell from the microfluidic device.

As used in the present specification and in the appended claims, the term "cell" is meant to be understood as a living organism that can replicate independently.

Additionally, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may or may not be included in other examples.

Turning now to the figures, FIG. 1 is a block diagram of a microfluidic device (100) according to an example of the principles described herein. The microfluidic device (100) may include at least one microfluidic channel (105), a dielectrophoresis separator (110), and a thermal resistor (115). The microfluidic device (100) may be formed into a cassette that interfaces with a fluid ejection device. As will be described herein, the microfluidic device (100) in the form of a cassette may receive electrical signals and voltages that cause at least, the dielectrophoresis separator (110) to separate a plurality of cells passing within the at least one microfluidic channel (105) as well as cause the thermal resistor (115) to be activated in order to eject a cell from the microfluidic device (100).

The microfluidic channel (105) may be of any length that allows a plurality of cells from a sample to be passed therethrough an into the dielectrophoresis separator (110). The microfluidic channel (105) may fluidically couple the dielectrophoresis separator (110) to a number of inlets. The number of inlets may include at least one sample inlet. The sample inlet contains a plurality of cells to be eventually separated from each other downstream using the dielectrophoresis separator (110). In an example, a number of sheath fluid inlets may also be included upstream of the microfluidic channel (105) and may merge with the flow from the sample inlet upstream of the dielectrophoresis separator (110). The sheath fluid provided via the sheath fluid inlets may be any type of fluid that provides a flow through the microfluidic channel (105) and dielectrophoresis separator (110) and, in some examples, may cause the plurality of cells to generally line up while passing through the dielectrophoresis separator (110). The laminar flow created by the sheath fluid may provide for relatively easier separation of the plurality of cells in the dielectrophoresis separator (110).

The dielectrophoresis separator (110) implements an electrical field on the plurality of cells in order to force the cells to be separated from each other and pass into different outlet microfluidic channels (105) and away from the dielectrophoresis separator (110). In order for the electrical field to affect the plurality of cells, the cells do not have to be charged at all. Instead, because the cells exhibit di electrophoretic activity in the presence of electric field, the different types of cells may react differently in the presence of the electrical field and are thereby separated as the travel through the dielectrophoresis separator (110).

The microfluidic channels (105) may further direct separated cells generally to one of two different outlets. One or a plurality of types of cells may be directed to a waste outlet. The waste outlet may include a location within the microfluidic device (100) where cells not to be analyzed or otherwise ejected from the microfluidic device (100) may be maintained.

At least one type of cell may be directed to a firing chamber defined in the microfluidic device (100) that contains a thermal resistor (115). In an example, the thermal resistor (115) may eject from the microfluidic device (100) one cell at a time. The cells may be specifically ejected into a well defined within a well plate. The microfluidic device (100) may have at least one nozzle defined therein through which the cell may be ejected from the microfluidic device (100) using the thermal resistor (115).

In an example, a number of sense electrodes may be placed upstream of the firing chamber and thermal resistor (115). The sense electrode may, in an example, detect at least the presence of a cell as it passes from the dielectrophoresis separator (110) and into the firing chamber. In an example, the sense electrode may detect the type of cell passing from the dielectrophoresis separator (110) into the firing chamber. In an example, the microfluidic device (100) may further cause some cells to be ejected into a spittoon defined on the well plate. In this example, the cells ejected into the spittoon have been detected by the sense electrode to be a type of cell to not be analyzed within a well within the well plate. In this example, the cell that is not to be analyzed may have mistakenly made it into the microfluidic channel (105) leading to the firing chamber. The sense electrode discovers this, and notifies, for example, a fluid ejection device that the cell in the firing chamber at any given time is a type of cell to not be analyzed. Upon receipt of this indication, the fluid ejection device causes the microfluidic device (100) and thermal resistor (115) to eject the cell into the spittoon instead of a well.

As mentioned above, the microfluidic device (100) may interface with a fluid ejection device that directs, at least, the dielectrophoresis separator (110) to separate a plurality of cells and the thermal resistor (115) to eject at least one cell from the microfluidic device (100). In order to accomplish this, the microfluidic device (100) may include a number of electrical traces that electrically couple the dielectrophoresis separator (110) and thermal resistor (115) to a voltage source provided by the fluid ejection device. These electrical traces may be built within the microfluidic device (100) and/or defined on a number of surfaces of the microfluidic device (100). The fluid ejection device may interface with these electrical traces to provide the voltage as described herein.

The thermal resistor (115) may be any type of device that may heat up a portion of a liquid in order to eject at least one cell in that liquid out of a firing chamber defined in the microfluidic device (100). To do so, the thermal resistor (115) may be electrically coupled to a voltage source via the electrical traces described herein. It is to be understood that the thermal resistor (115) is merely an example of a device that may eject a liquid and/or cell from the microfluidic device (100) and the present specification contemplates that use of any type of ejection device that may be used to eject the cell.

Figure 2:
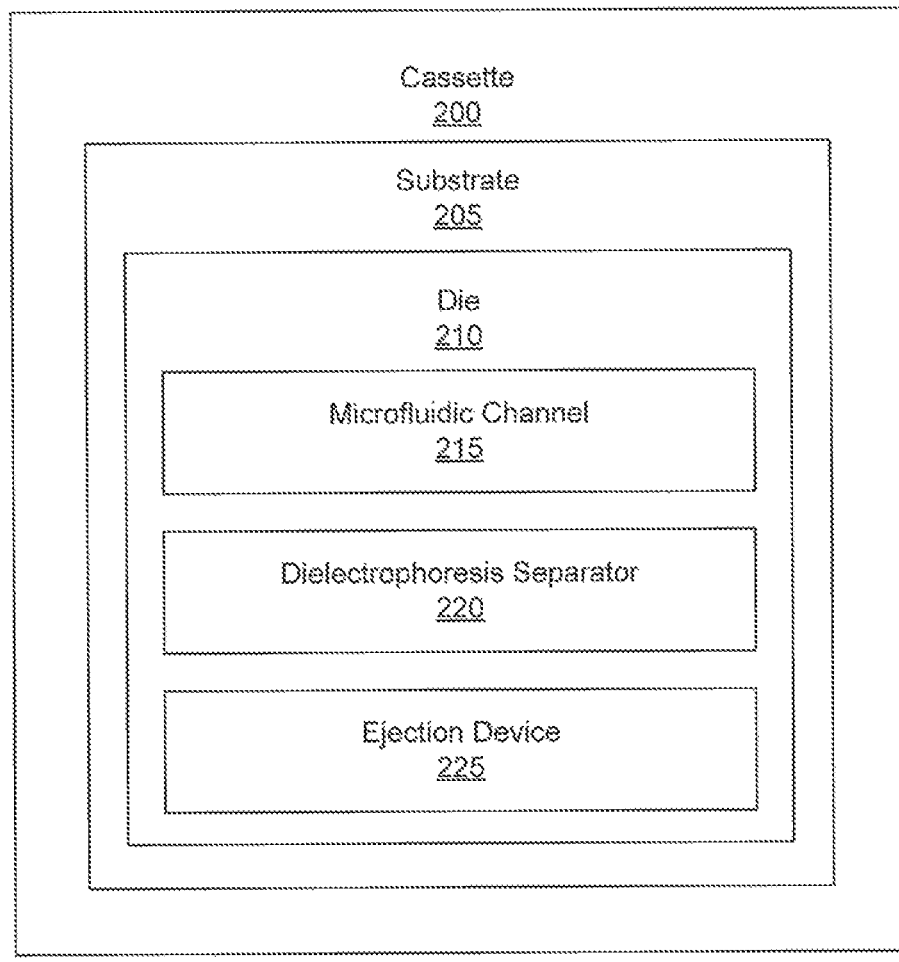
FIG. 2 is a block diagram of a cassette according to an example of the principles described herein.

FIG. 2 is a block diagram of a cassette (200) according to an example of the principles described herein. The cassette (200) may include a die (210) coupled to a substrate (205) of the cassette (200). The die (210) may include at least one microfluidic channel (215) defined therein, a dielectrophoresis separator (220) to separate a plurality of cells from each other, and an ejection device (225) to eject at least one cell from the die (210) and cassette (200).

The substrate (205) of the cassette (200) may be made of any resilient material that may interface with a fluid ejection device as described herein. In an example, the substrate (205) may be made of a thermoplastic material. In this example, the thermoplastic material may be doped with a non-conductive, metallic, inorganic compound. In this example, a number of metal traces may be added to any surface of the cassette (200) using a laser direct structuring (LDS) process. During the LDS process, the non-conductive, metallic, inorganic compounds are activated by a laser providing a surface into which a layer of conductive metal may be deposited using, for example, an electroless copper bath. The metallic layers may also be in electrical communication with a number of die pads formed on an exterior surface of the die (210). The die pads provide an electrical interface between a number of electrical traces formed on the surface of the substrate (205) so that electrical pulses and/or voltages may be provided to the ejection device (225), other microfluidic devices, and or the dielectrophoresis separator (220) during operation of the cassette (200).

In an example, the die (210) is coupled to a surface of the substrate (205). Opposite the surface of the substrate (205) where the die (210) has been coupled, a reservoir may be formed to receive a sample containing cells. In this example, the reservoir may provide access to a user in order for the user to deposit the fluid containing cells in the reservoir for eventual cell delivery to the die (210) through a slot defined in the substrate (205) between the reservoir and die (210). As described above, the die (210) may further include a sample inlet that receives the fluid containing cells from the slot and reservoir.

The electrical traces defined on the surface of the substrate (205) may further include a number of connection pads used to interface with a fluid ejection device. These connection pads may interface with, for example, a number of pogo connectors of a printed circuit assembly (PCA) of the fluid ejection device. This allows the cassette (200) to interface with the fluid ejection device and be used by the fluid ejection device to selectively eject cells from the die (210) and into a well plated presented below the cassette (200).

The dielectrophoresis separator (220) may be similar to the dielectrophoresis separator (FIG. 1, 110) described in connection with FIG. 1. The dielectrophoresis separator (220) separates one cell from another based on a number of characteristics including type, size, and shape of each of the cells. The dielectrophoresis separator (220) may create an electric field tuned to separating the cells from each other based, at least, on one of these characteristics. As the dielectrophoresis separator (220) separates the cells according to one of these characteristics using the electric field, the cells may be fluidically moved to a microfluidic channel (215) leading to any number of outlets as described herein. One type of outlet includes a firing chamber housing the ejection device (225). As the separated cell travels towards the firing chamber, it may pass a sense electrode that can detect the characteristics of the cell passing by and determine whether to eject the cell into a well defined in a well plate or into a waste spittoon. In either case, the cell may reach the ejection chamber and be ejected from the die (210) using the ejection device (225).

The ejection device (225) may be any type of device that can eject a cell from the die (210) of the cassette (200). Examples of types of ejection devices may include thermoresistive devices and piezoelectric devices. In an example, the ejection device (225) is a piezoelectric device as opposed to a thermoresistive device when the cell is not to be heated before being deposited into the well of the well plate. In some examples, a thermoresistive device may be implemented as the ejection device (225) for the dual purpose of preparing the cell through heating as well as ejection from the die (210).

Figure 3:
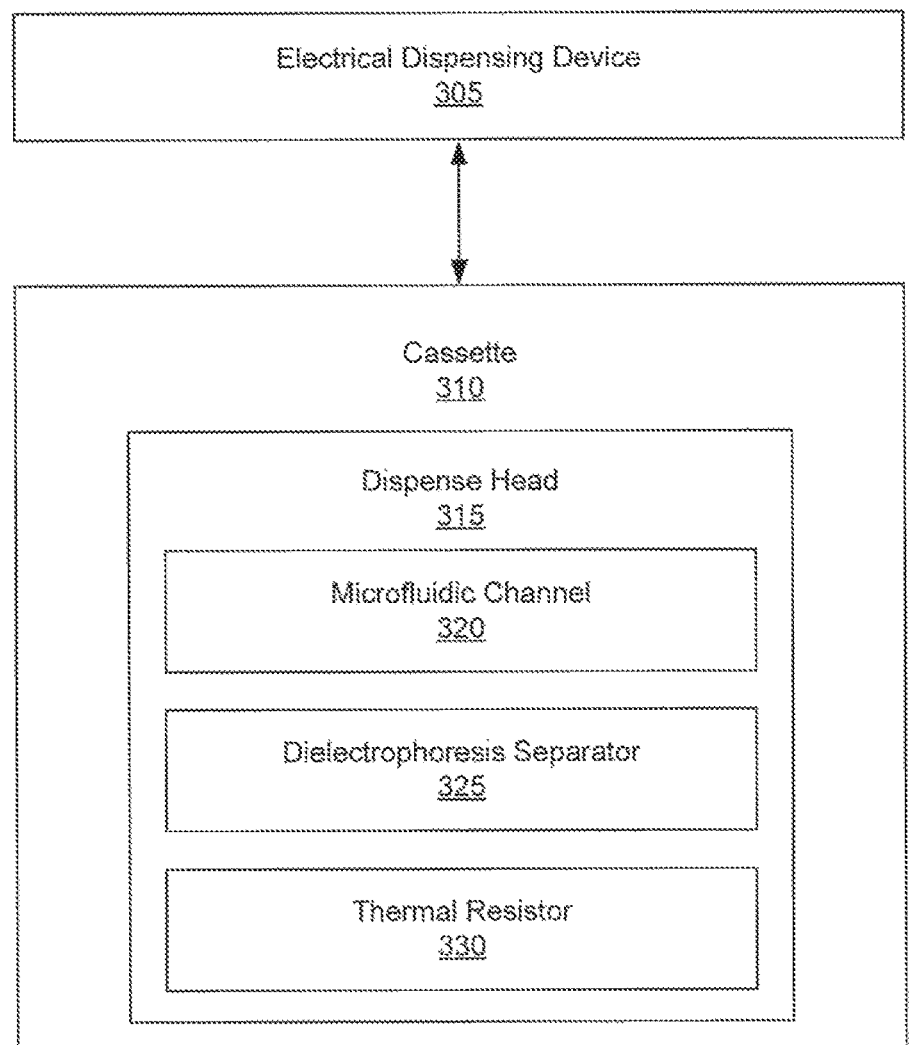
FIG. 3 is a block diagram of the fluid ejection system according to an example of the principles described herein.

FIG. 3 is a block diagram of the fluid ejection system (300) according to an example of the principles described herein. The fluid ejection system (300) may include an electrical dispensing device (305) and a cassette (310) to selectively interface with the electrical dispensing device (305). The cassette (310) may include a dispense head (315) having at least one microfluidic channel (320), a dielectrophoresis separator (325), and a thermal resistor (330).

The electrical dispensing device (305) may be any device that provides an electrical voltage to at least the dielectrophoresis separator (325) and thermal resistor (330) of the dispense head (315) and selectively move the cassette (310) over a well plate in order to cause a cell to be ejected from the dispense head (315) using the thermal resistor (330). In an example, the electrical dispensing device (305) may cause a single cell to be ejected from the dispense head (315). In an example, the dispense head (315) may eject a number of cells into the well plate one cell at a time. In another example, the electrical dispensing device (305) may cause the thermal resistor (330) to eject a plurality of cells at a time into a well of the well plate.

The electrical dispensing device (305) may be communicatively coupled to a computing device. Example computing devices include servers, desktop computers, laptop computers, personal digital assistants (PDAs), mobile devices, smartphones, gaming systems, and tablets, among other computing devices.

The electrical dispensing device (305) may be utilized in any data processing scenario including, stand-alone hardware, mobile applications, through a computing network, or combinations thereof. Further, the electrical dispensing device (305) may be used in a computing network, a public cloud network, a private cloud network, a hybrid cloud network, other forms of networks, or combinations thereof. The present systems may be implemented on one or multiple hardware platforms, in which the modules in the system can be executed one or across multiple platforms. Such modules can run on various forms of cloud technologies and hybrid cloud technologies or offered as a SaaS (Software as a service) that can be implemented on or off the cloud. In another example, the methods provided by the fluid ejection system (300) are executed by a local administrator.

To achieve its desired functionality, the electrical dispensing device (305) comprises various hardware components. Among these hardware components may be a number of processing devices, a number of data storage devices, a number of peripheral device adapters, and a number of network adapters. These hardware components may be interconnected through the use of a number of busses and/or network connections. In one example, the processor, data storage device, peripheral device adapters, and network adapter may be communicatively coupled via a bus within the electrical dispensing device (305).

The processor may include the hardware architecture to retrieve executable code from the data storage device and execute the executable code. The executable code may, when executed by the processor, cause the processor to implement at least the functionality of sending a voltage to at least the dielectrophoresis separator (325) and/or thermal resistor (330), according to the methods of the present specification described herein. In the course of executing code, the processor may receive input from and provide output to a number of the remaining hardware units.

The data storage device may store data such as executable program code that is executed by the processor or other processing device. The data storage device may specifically store computer code representing a number of applications that the processor executes to Implement at least the functionality described herein.

The data storage device may include various types of memory modules, including volatile and nonvolatile memory. For example, the data storage device of the present example includes Random Access Memory (RAM). Read Only Memory (ROM), and Hard Disk Drive (HDD) memory. Many other types of memory may also be utilized, and the present specification contemplates the use of many varying type(s) of memory in the data storage device as may suit a particular application of the principles described herein. In certain examples, different types of memory in the data storage device may be used for different data storage needs. For example, in certain examples the processor may boot from Read Only Memory (ROM), maintain nonvolatile storage in the Hard Disk Drive (HDD) memory, and execute program code stored in Random Access Memory (RAM).

Generally, the data storage device may comprise a computer readable medium, a computer readable storage medium, or a non-transitory computer readable medium, among others. For example, the data storage device may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store computer usable program code for use by or in connection with an instruction execution system, apparatus, or device. In another example, a computer readable storage medium may be any non-transitory medium that can contain, or store a program for use by or in connection with an instruction execution system, apparatus, or device.

The hardware adapters in the electrical dispensing device (305) enable the processor to interface with various other hardware elements, external and internal to the electrical dispensing device (305). For example, the peripheral device adapters may provide an interface to input/output devices, such as, for example, display device, a mouse, or a keyboard. The peripheral device adapters may also provide access to other external devices such as an external storage device, a number of network devices such as, for example, servers, switches, and routers, client devices, other types of computing devices, and combinations thereof.

The display device may be provided to allow a user of the electrical dispensing device (305) to interact with and implement the functionality of the electrical dispensing device (305) as described herein. The peripheral device adapters may also create an interface between the processor and the display device or other media output devices. The network adapter may provide an interface to other computing devices within, for example, a network, thereby enabling the transmission of data between the electrical dispensing device (305) and other devices located within the network.

The electrical dispensing device (305) may, when executed by the processor, display the number of graphical user interfaces (GUIs) on the display device associated with the executable program code representing the number of applications stored on the data storage device. The GUIs may include aspects of the executable code including the presentation of different ejection criteria and/or processes to be conducted based on the type of cells to be ejected from the dispense head (315) of the cassette (310).

The dispense head (315) may be similar to the die (FIG. 2, 210) described above in connection with FIG. 2. Specifically, the dispense head (315) may include at least one microfluidic channel (320) fluidically coupling a sample inlet to the dielectrophoresis separator (325) and the dielectrophoresis separator (325) to a number of fluid outlets as described herein. The dispense head (315) may include any number of fluid inlets including a sample inlet and a sheath fluid inlet. The dispense head (315) may include any number of outlets including a waste cell outlet leading to a waste depository defined within the dispense head (315) and a test cell outlet leading to a firing chamber housing the thermal resistor (330) for eventual ejection from the dispense head (315) into a substrate such as a well plate.

The cassette (310) and its dispense head (315) may be caused to be selectively engaged with the electrical dispensing device (305). Engaging the cassette (310) with the electrical dispensing device (305) may cause a number of electrical traces and/or pads formed between the cassette (310) and dispense head (315) and on the cassette (310) itself to electrically communicate with electrical connectors of the electrical dispensing device (305). In this way, the electrical dispensing device (305) may provide signals and voltages to the cassette (310) via the electrical traces and pads as described herein.

Any number of cassettes (310) may interface with the electrical dispensing device (305) at any given time or for any duration. In some examples, the cassettes (310) may be disposable thereby decreasing the possibility of cross-contamination between different testing procedures of cell samples.

The electrical dispensing device (305) may further maintain a substrate onto which the cells ejected from the dispense head (315) of the cassette (310) may be placed. In an example, the substrate is a well plate with a number of wells defined therein. During operation, the electrical dispensing device (305) may direct or move the cassette (310), and specifically the dispense head (315), over a certain location of the well plate so as to be able to eject at least one cell into one of the wells.

Figure 4:
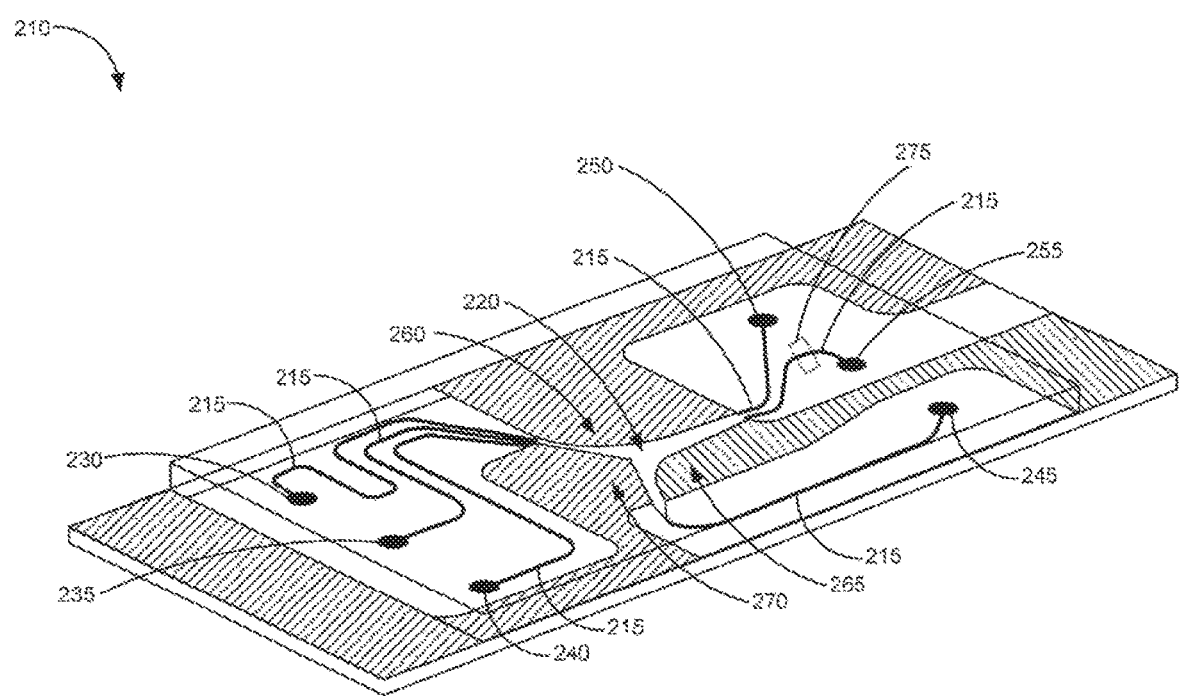
FIG. 4 is a perspective cutout view of the die of FIG. 2 according to an example of the principles described herein.

FIG. 4 is a perspective cutout view of the die (210) of FIG. 2 according to an example of the principles described herein. In an example, the die (210) shown is FIG. 2 is a portion of a larger die. In this example, the microfluidic channel (215), dielectrophoresis separator (220), and/or ejection device (225) may be provided multiple times within a single die (210), the portion of the die (210) being shown in FIG. 2.

As described above, the die (210) includes at least one microfluidic channel (215). A number of microfluidic channels (215) may fluidically couple a number of sheath fluid inlets (230, 240) to the dielectrophoresis separator (220). As described herein, the sheath fluid inlets (230, 240) may provide a sheath fluid to a culmination portion of the microfluidic channels (215) provided upstream of the dielectrophoresis separator (220). A number of microfluidic channels (215) may also fluidically couple a sample inlet (235) to the dielectrophoresis separator (220). The sample inlet (235) may provide a sample including a plurality of cells to a culmination portion of the microfluidic channels (215) upstream of the dielectrophoresis separator (220).

In an example, the microfluidic channels (215) immediately downstream of the sheath fluid inlets (230, 240) and sample inlet (235) may merge together before reaching the dielectrophoresis separator (220). The allows the sheath fluid and sample containing cells to mix before the dielectrophoresis separator (220) applies the electric filed on the mixture.

As the mixture of sheath fluid and sample with cells enter the dielectrophoresis separator (220), the electric filed applies a force on each of the cells thereby separating them into a number of microfluidic channels (215) downstream of the dielectrophoresis separator (220). The application of the electric field may influence different types and sizes of cells differently leading to the separation of the cells from each other.

The dielectrophoresis separator (220) may have a first electrode (260), a second electrode (265), and a ground (270) that creates the electric field within the dielectrophoresis separator (220). As described herein the voltages applied to the first and second electrodes (260, 265) may be provided using a voltage source associated with an electrical dispensing device (FIG. 3, 305).

As the cells exit the dielectrophoresis separator (220) they are in a separated state and flow into a number of outlets based on whether the cells are to be ejected from the die (210) or not. The cells that are not to be ejected from the die (210) and, consequently, not to be part of a diagnostic process at the well plate, may be directed to a waste outlet (245). The waste outlet (245) may be a cavity defined within the die (210) that may hold an amount or number of cells therein. The cells to be ejected may be sent towards a test cell outlet (255). The test cell outlet (255) may be or may further lead to a firing chamber in which the ejection device (225) may be placed. The ejection device (225) may then eject the cell from the die (210) as described herein. Different types of cells may further be lead to an analysis outlet (250). The analysis outlet (250) may be an outlet where cells to be tested within the die (210) may be directed. Any type of in-die (210) analysis may be made and the present specification contemplates those devices used to complete those analysis.

The microfluidic channel (215) leading from the dielectrophoresis separator (220) to the sample inlet (235) may further include a sense electrode (275). The sense electrode (275) may sense both the presence of a cell as well as the type and/or characteristics of the cell. On some occasions, cells not to be ejected may have gone down the microfluidic channel (215) leading to the test cell outlet (255). In this case, the sense electrode (275) can detect the presence of that cell and indicate to the electrical dispensing device (FIG. 3, 305) indicating such presence. The electrical dispensing device (FIG. 3, 305) may then direct the die (210) to eject the cell, not into a well of the well plate, but instead into a spittoon.

Figure 5A:
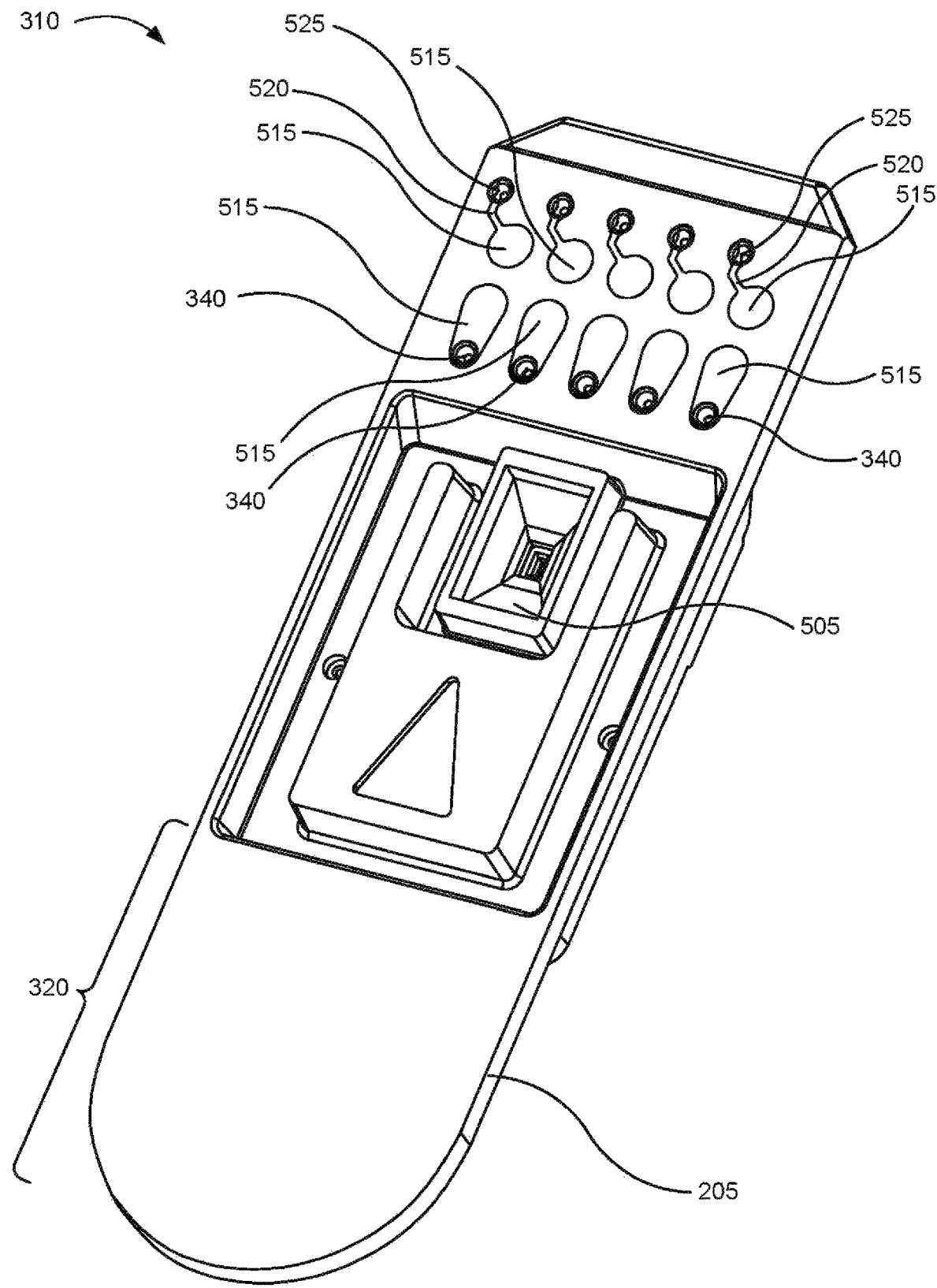
FIGS. 5A and 5B are a front and rear perspective views, respectively of a cassette according to an example of the principles described here.
Figure 5B:
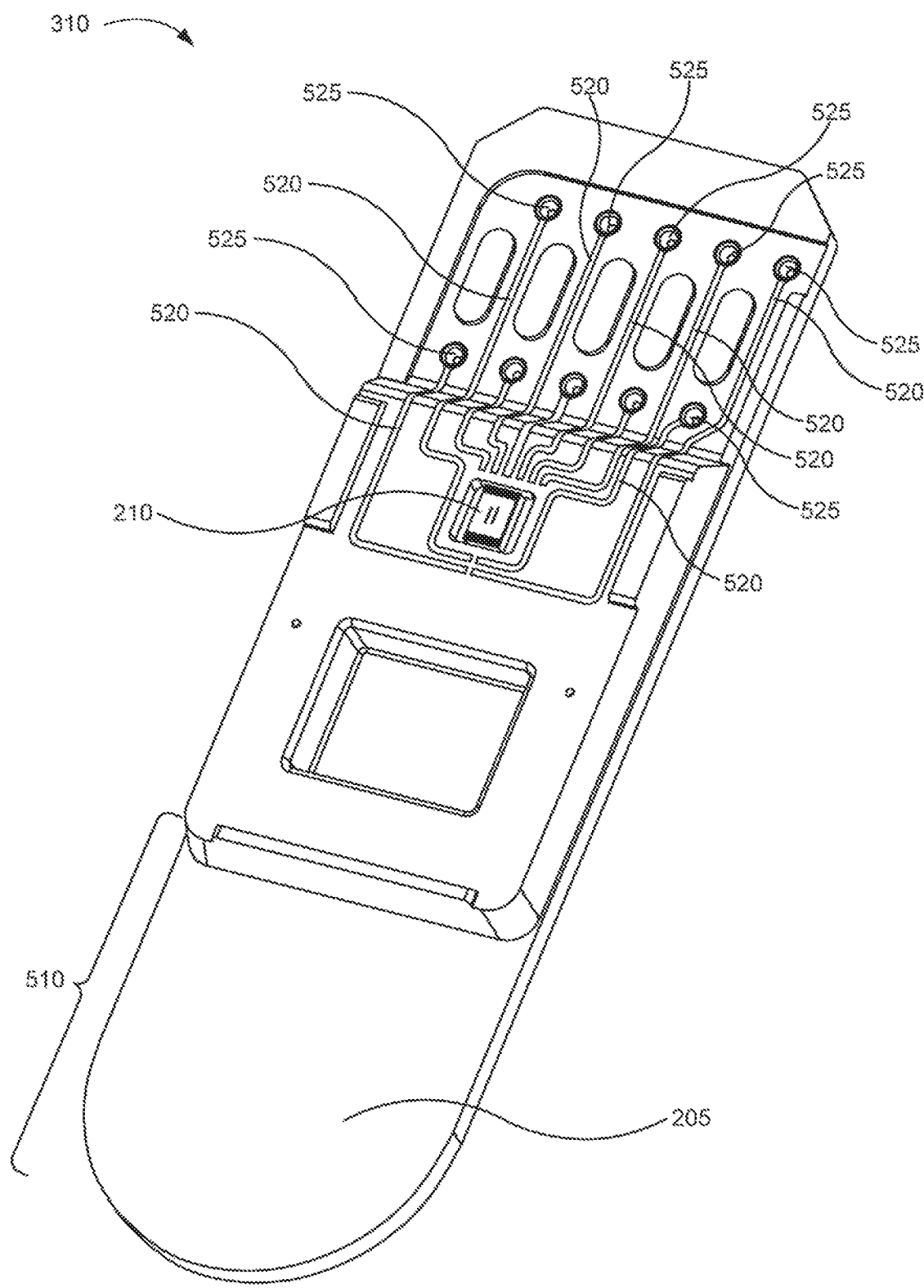

FIGS. 5A and 5B are a front and rear perspective views, respectively of a cassette (310) according to an example of the principles described here. As described above, the cassette (310) includes a substrate (205), a die (210) coupled to the substrate (205), and a reservoir (505) defined in the substrate (205). The cassette (310) with its substrate (205), die (210), and reservoir (505) may all be similar to those elements as described herein.

The substrate (205) may be formed to allow a user to insert or otherwise interface the cassette (310) with a system for ejecting a fluid into an assay such as the electrical dispensing device (FIG. 3, 305). In the example show in FIG. 5, the substrate (205) may include a handle (510). The handle (510) allows a user to grip the cassette (310) in order to manipulate the cassette (310) and place the cassette (310) into the system used to eject a fluid into an assay.

The cassette (310) may further include a number of connection pads (515) and electrical traces (520) so that the die (210) of the cassette (310) can receive electrical signals directing when, where, and how to eject an amount of fluid and/or cell therefrom. In an example, the cassette (310) is moved relative to an assay plate positioned below the cassette (310) such that placement of the die (210) over any portion of the assay plate and ejection of fluid and/or cells from the die (210) allows an amount of fluid and/or cells to be ejected into any number of wells formed in the assay plate. The ejection of the fluid from the die (210) is directed by a controller of the electrical dispensing device (FIG. 3, 305) for ejecting a fluid into an assay as described above.

Thus, in order to allows the cassette (310) to interface with the electrical dispensing device (FIG. 3, 305), the cassette (310) may include a number of connection pads (515) that interface with, for example, a number of pogo connectors on a printed circuit assembly (PCA) of the electrical dispensing device (FIG. 3, 305). In the examples shown the figures of the present description the number of connection pads (515) is ten. However, the present specification contemplates the use of less or more connection pads (515). The number of connection pads (515) may be varied among different examples because the die (210) may receive signals from the PCA directing a number of microelectromechanical systems (MEMS) devices to be activated. Consequently, more or less connection pads (515) may be added or subtracted from those shown in FIGS. 5A and 5B based on the number of signals used to activate any number of MEMS devices within the die (210). Not all of the connection pads (515) have been indicated in FIGS. 5A and 5B in order to allow for better understanding of the cassette (310).

In an example, a number of electrical traces (520) may electrically couple each of the connection pads (515) to a via (525). In other examples, the connection pads (515) themselves may be electrically coupled to the their respective vias (525) without the use of traces (520).

In an example, the connection pads (515) and electrical traces (520) may be formed onto the surface of the substrate (205) using a LDS process. Again, during the LDS process, the non-conductive, metallic, inorganic compounds are activated by a laser providing a surface into which a layer of conduct metal may be deposited using, for example, an electroless copper bath. The vias (525) may provide an electrical connection to a number of other electrical traces (520) formed on an opposite side of the cassette (300).

The systems and devices described herein provide for the separation and arraying of cells, especially relatively rarer cells, thereby furthering the medicine and biology fields. Such separation of cells allows biologist and clinical scientists to sequence of DNA and RNA, or mass spectroscopic analysis of the proteins of the single cells and, consequently allows them to understand how cells work on the individual level as well as how the heterogeneity of such behavior contributes to the function of the overall tissue.

Such separations of cells are also used for diagnostics of diseases, especially those driven by the relatively rarer cells. An example of such disease is cancer, which is driven by circulating tumor cells in the patients' blood. Circulating tumor cells are responsible for metastasis and the metastasis in turn is what causes medical complications for cancer patients'. Detection, separation, and analysis of these metastasis cells provide benefits in cancer research.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general-purpose computer, special purpose computer, or other programmable data processing apparatus to produce a machine, such that the computer usable program code, when executed via, for example, the processor of the electrical dispensing device (FIG. 3, 305) or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The preceding description has been presented to illustrate and describe examples of the principles described. This description is not intended to be exhaustive or to limit these principles to any precise form disclosed. Many modifications and variations are possible in light of the above teaching.

What is claimed is:

1. A microfluidic device, comprising:
   a dielectrophoresis separator;
   a first plurality microfluidic channels, at least one of the first plurality configured to pass a fluid and at least one of the first plurality configured to pass a sheath fluid to the dielectrophoresis separator;
   the dielectrophoresis separator fluidically coupled the first plurality of microfluidic channels and configured to separate a plurality of cells;
   a number of outlets;
   a second plurality of microfluidic channels fluidically coupled to the dielectrophoresis separator and configured to direct fluid exiting the dielectrophoresis separator to the number of outlets, the number of outlets are respectively fluidically coupled to the second plurality of microfluidic channels and comprise a firing chamber; and the firing chamber comprises a thermal resistor configured to eject at least one cell of the plurality of cells, the firing chamber being fluidically coupled to one of the second plurality of microfluidic channels.

2. The microfluidic device of claim 1, further comprising a sense electrode downstream of the dielectrophoresis separator and configured to detect a presence of at least one cell of the plurality of cells in one of the second plurality of microfluid channels.

3. The microfluidic device of claim 1, further comprising multiple sheath fluid inlets each fluidically coupled to a respective corresponding one of the first plurality of microfluidic channels, the multiple sheath fluid inlets configured to provide a sheath fluid flow to the respective corresponding one of the first plurality of microfluidic channel channels.

4. The microfluidic device of claim 3, further comprising a sample inlet fluidically coupled to a respective one of the first plurality of microfluidic channels, the sample inlet configured to provide a flow of cells through the respective one of the first plurality of microfluidic channel channels wherein the sample inlet is different from the multiple sheath inlets.

5. The microfluidic device of claim 1, wherein the number of outlets comprises a waste outlet and a test cell outlet.

6. The microfluidic device of claim 1, wherein the second plurality of microfluidic channels comprises a first microfluidic channel leading away from the dielectrophoresis separator and a second microfluidic channel leading away from the dielectrophoresis separator.

7. The microfluidic device of claim 6, the number of outlets comprises at least two outlets;
wherein the first microfluidic channel and the second microfluidic channel leading away from the dielectrophoresis separator each leads to a respective one of the at least two outlets.

8. The microfluidic device of claim 7, wherein one of the least two outlets comprises a test cell outlet and another one of the at least two outlets comprises an analysis outlet.

9. The microfluidic device of claim 2, wherein the thermal resistor is configured to ejects the at least one cell in response to the at least one cell being detected as being present in one of the plurality of second microfluidic channels by the sense electrode, and the sense electrode indicates that the at least one cell of the plurality of cells is not of a type of cell to be analyzed.

10. The microfluidic device of claim 4, wherein the multiple sheath fluid inlets and sample inlet merge in a culmination portion of the first plurality of microfluidic channels.

11. A cassette, comprising:
a substrate;
a die coupled to the substrate, the die comprising:
a sample inlet;
multiple sheath fluid inlets, different from the sample inlet;
a dielectrophoresis separator;
a first plurality of microfluidic channels respectively fluidically coupled to the sample inlet and the multiple sheath fluid inlets and respectively configured to pass a fluid and sheath fluid from the sample inlet and the multiple sheath fluid inlets to the dielectrophoresis separator;

the dielectrophoresis separator fluidically coupled to the first plurality of microfluidic channels and configured to separate a plurality of cells;

a number of outlets;

a second plurality of microfluidic channels fluidically coupled to the dielectrophoresis separator and configured to direct fluid exiting the dielectrophoresis separator to the number of outlets, the number of outlets are respectively coupled to the second plurality of microfluidic channels and comprise a firing chamber; and the firing chamber comprises an ejection device configured to eject at least one of the plurality of cells, the firing chamber being fluidically coupled to one of the second plurality of microfluidic channels.

12. The cassette of claim 11, further comprising a test cell outlet; wherein one of the second plurality of microfluidic channels microfluidic channels is fluidically coupled to the test cell outlet.

13. The cassette of claim 12, wherein each of the second plurality of microfluidic channels includes a sense electrode to sense a cell within each of the second plurality of microfluidic channels.

14. The cassette of claim 12, further comprising a waste outlet; wherein one of the second plurality of microfluidic channels is fluidically coupled to the waste outlet.

15. The cassette of claim 12, further comprising an analysis outlet; wherein one of the second plurality of microfluidic channels is fluidically coupled to the analysis outlet.

16. A fluid ejection system comprising:
the cassette of claim 11, further comprising a number of electrical connection pads defined on a surface of the cassette; and
an electrical dispensing device connected to the number of electrical connection pads.

17. The fluid ejection system of claim 16, wherein the electrical dispensing device provides a voltage to the dielectrophoresis separator via the number of electrical connection pads.

18. A method, comprising:
passing a sample including a plurality of cells from a sample inlet to a first one of a first plurality of microfluidic channels that is fluidically coupled to the sample inlet; wherein each of the first plurality of microfluidic channels is fluidically coupled to a dielectrophoresis separator;
passing a sheath fluid from a first sheath fluid inlet and a second sheath fluid inlet to a second and third of the first plurality of microfluidic channels that are fluidically coupled to the first sheath fluid inlet and second sheath fluid inlet respectively and are fluidically coupled to the dielectrophoresis separator;
merging the sample and the sheath fluid from the respective first plurality of microfluidic channels before reaching the dielectrophoresis separator;
providing the merged sample and sheath fluid to the dielectrophoresis separator;
creating an electrical field in the dielectrophoresis separator configured to separate the plurality of cells by type;
directing from the dielectrophoresis separator a first type of cell of the plurality of cells to a firing chamber that comprises a thermal resistor via a first one of a second plurality of microfluidic channels coupled to the dielectrophoresis separator;

directing from the dielectrophoresis separator a second type of cell of the plurality of cells to a waste outlet via a second one of the second plurality of microfluidic channels; and directing from the dielectrophoresis separator a third type of cell of the plurality of cells to an analysis outlet via a third one of the second plurality of microfluidic channels.

19. The method of claim 18, wherein the first sheath fluid inlet is disposed on a first side of the sample inlet and the second sheath fluid inlet is disposed on a second side of the sample inlet.

* * * * *